(12) United States Patent
Stendel et al.

(10) Patent No.: US 8,394,397 B2
(45) Date of Patent: Mar. 12, 2013

US008394397B2

(54) ADHESIVE ANTINEOPLASTIC COMPOSITIONS

(75) Inventors: Ruediger Stendel, Berlin (DE); Rolf W. Pfirrmann, Lucerne (CH)

(73) Assignee: Ed. Geistlich Soehne AG fuer Chemische Industrie, Wolhusen (CH)

(*) Notice: Subject to any disclaimer, the term of this patent is extended or adjusted under 35 U.S.C. 154(b) by 1248 days.

(21) Appl. No.: 10/809,920

(22) Filed: Mar. 26, 2004

(65) Prior Publication Data

US 2004/0220181 A1 Nov. 4, 2004

Related U.S. Application Data

(60) Provisional application No. 60/457,924, filed on Mar. 28, 2003.

(51) Int. Cl.
*A61F 13/00* (2006.01)
(52) U.S. Cl. .................................................. 424/422
(58) Field of Classification Search .................. None
See application file for complete search history.

(56) References Cited

U.S. PATENT DOCUMENTS

| | | | | |
|---|---|---|---|---|
| 4,587,268 A * | 5/1986 | Pfirrmann | ..................... | 514/774 |
| 4,772,468 A | 9/1988 | Pfirrmann | | |
| 5,210,083 A | 5/1993 | Pfirrmann | | |
| 5,433,958 A * | 7/1995 | Grislain et al. | ............... | 424/436 |
| 5,593,665 A | 1/1997 | Pfirrmann et al. | | |
| 5,749,895 A * | 5/1998 | Sawyer et al. | ................. | 606/214 |
| 5,750,657 A * | 5/1998 | Edwardson et al. | .......... | 530/382 |
| 5,788,979 A * | 8/1998 | Alt et al. | ....................... | 424/426 |
| 5,819,748 A * | 10/1998 | Pfirrmann | ..................... | 128/898 |
| 6,080,397 A * | 6/2000 | Pfirrmann | .................. | 424/78.08 |
| 6,258,797 B1 * | 7/2001 | Lehner | ............................ | 514/56 |
| 6,296,831 B1 | 10/2001 | Weller et al. | | |
| 6,429,224 B1 | 8/2002 | Calabresi et al. | | |
| 6,479,481 B1 | 11/2002 | Stendel et al. | | |
| 6,488,912 B1 | 12/2002 | Pfirrmann et al. | | |
| 6,521,616 B2 | 2/2003 | Calabresi et al. | | |
| 6,841,617 B2 | 1/2005 | Jeong et al. | | |
| 6,869,588 B2 | 3/2005 | Weller et al. | | |
| 6,919,067 B2 * | 7/2005 | Filler et al. | .................. | 424/1.29 |
| 7,087,244 B2 | 8/2006 | Jeong et al. | | |
| 2001/0031870 A1 | 10/2001 | Soll et al. | | |
| 2002/0111345 A1 | 8/2002 | Calabresi et al. | | |
| 2002/0131935 A1 | 9/2002 | Fisher et al. | | |
| 2006/0141007 A1 * | 6/2006 | Beisel | .......................... | 424/439 |

FOREIGN PATENT DOCUMENTS

| | | |
|---|---|---|
| GB | 1 557 163 | 12/1979 |
| JP | 05-29484 A | 11/1993 |
| JP | 05-294849 A * | 11/1993 |
| JP | 10-45616 A | 2/1998 |
| JP | 10-236984 A | 9/1998 |
| WO | WO 92/00743 A1 | 1/1992 |
| WO | 01/39762 A2 | 6/2001 |
| WO | 01/39762 A3 | 6/2001 |
| WO | WO 01/39763 A2 | 6/2001 |
| WO | WO 0139762 A2 * | 6/2001 |
| WO | WO 0139763 A2 * | 6/2001 |

OTHER PUBLICATIONS

Wicki et al., "35. *Surgical Irrigation Solutions*", 244-253, 1985 (with English translation).

Blenkharn, J.I., "*The Differential Cytotoxicity of Antiseptic Agents*", J. Pharm. Pharmacol., 39:477-479, 1987.

Blenkharn, J.I., Manuscript: "*The Differential Cytotoxicity of Taurolin and Noxythiolin*", 8 pages, Jul. 22, 1986.

Zimmerman, M., et al., "*The antimicrobial actions of Taurolin and other preparations on the pathogenic spectrum in dentoalveolar infections*", Int. J. of Clinical Therapy and Toxicology, 31:3, 130-136, 1993.

Semple, J., et al., "Potent and selective thrombin inhibitors featuring hydrophobic, basic $P_3$-$P_4$-aminoalkyllactam moieties", *Bioorganic & Medicinal Chemistry Letters 8*, 1998; pp. 3525-3530.

Bedrosian, I., et al., "Taurolidine, an Analogue of the Amino Acid Taurine, Suppresses Interleukin 1 and Tumor Necrosis Factor Synthesis in Human Peripheral Blood Mononuclear Cells", *Cytokine* vol. 3, No. 6 (Nov.) 1991: 568-575.

Clark, K., et al., "KRN8602 (MX2-hydrochloride): an Active New Agent for the Treatment of Recurrent High-grade Glioma", *J. Clin. Oncol.*, Aug. 1999, 17 (8): 2579-84, PUBMED Abstract.

Dimmock, Jr, et al., "Mannich Bases of Phenolic Azobenzenes Possessing Cytotoxic Activity", *Eur. J. Med. Chem.* (1997) 32, 583-594.

Jacobi, C.A., et al., "Intraperitoneal Instillation of Taurolidine and Heparin for the Prevention of Intraperitoneal Tumor Growth and Trocar Metastases in Laparoscopic Surgery in a Rat Model", *Lagenbecks Arch Chir* (1997) 382 [Suppl.1]: S31-S36.

Jacobi, C.A., et al., "Inhibition of Peritoneal Tumor Cell Growth and Implantation in Laparoscopic Surgery in a Rat Model", *Am J of Surgery*, vol. 174, Sep. 1997: 359-363.

Monson, J.R.T., et al., "Taurolidine as an anti-neoplastic agent: a previously undiscovered role?", *Br. J. Surg.*, vol. 77, No. 12, Dec. 1990, 1432.

Monson, J.R.T., et al., "Preliminary Evidence that Taurolidine is anti-neoplastic as well as anti-endotoxin and anti-microbial", *Br. J. Surg.*, vol. 77, No. 6, Jun. 1990, A711.

Monson, J.R.T., et al., "Abrogation of tumor necrosis factor (TNF) toxicity in the murine model by taurolidine: support for synergism of TNF with endotoxin", *Br. J. Surg.*, vol. 77, No. 6, Jun. 1990, A708.

Monson, J.R.T., et al., "Taurolidine inhibits tumour necrosis factor (TNF) toxicity—new evidence in TNF and endotoxin synergy?", *Euro. J. Surg. Oncology*, 1993; 19:226-231.

(Continued)

*Primary Examiner* — Susan Tran
(74) *Attorney, Agent, or Firm* — Rothwell, Figg, Ernst & Manbeck, P.C.

(57) ABSTRACT

A method of treatment for preventing or inhibiting growth of cancer cells utilizes an antineoplastic composition including an antineoplastic-effective amount of a methylol transfer agent (MTA) in combination with biodegradable adhesive capable of adhering to tissue of a living subject.

4 Claims, No Drawings

OTHER PUBLICATIONS

Braumann, C., "Influence of Intraperitoneal and Systemic Application of Taurolidine and Taurolidine/Heparin During Laparoscopy on Intraperitoneal and Subcutaneous Tumour Growth in Rats," Clinical & Experimental Metastasis 18: 547-552, 2001, © 2001 Kluwer Academic Publishers, Printed in the Netherlands.

* cited by examiner

ADHESIVE ANTINEOPLASTIC COMPOSITIONS

CROSS-REFERENCE TO RELATED APPLICATION

This application claims the benefit of U.S. Provisional Application Ser. No. 60/457,924, filed Mar. 28, 2003.

BACKGROUND OF THE INVENTION

1. Field of the Invention

The present invention is in the field of antineoplastic compositions and methods.

2. Description of the Background Art

Taurolidine (Bis-(1,1-dioxoperhydro-1,2,4-thiadiazinyl-4)methane) was developed by Geistlich Pharma. It is a white crystalline substance, water soluble up to 2%. It is made up of two molecules of taurinamid and three molecules formaldehyde forming a two-ringed structure bridged by a methylene group.

Taurolidine has primarily an antibiotic and anti-endotoxin effect. It acts by a chemical reaction, so no microorganism resistance has been observed as yet. This effect of taurolidine is mediated by its active metabolites, which are donators of active methylol-groups: Methylol-Taurultam and Methylol-Taurinamide. The active methylol groups inactivate by reacting with the cell wall of bacteria and with the primary amino groups of endotoxins.

Additional effects of taurolidine were reported in the past: inhibition of TNF and IL-1 Beta in mononuclear cells (Bedrosian 1991), inhibition of Tumor Necrosis Factor Toxicity, and inhibition of Peritoneal Tumor Cell Growth in Laparoscopic Surgery (Jacobi 1997).

Taurolidine solutions have been used as instillation or rinsing solutions of the abdominal cavity in cases of peritonitis. In post-operative instillations, conscious patients have reported as a side-effect irritation and sometimes burning sensations.

Monson et al. PCT International Publication Number WO 92/00743 discloses a selective direct inhibiting effect of Taurolidine and/or Taurultam on certain body tumors. (Monson J R T, Ramsey P S, Donohue J H. Preliminary evidence that taurolidine is anti-neoplastic as well as anti-endotoxin and anti-microbial. Abstract. Br J Surg 77(6) 1990, A711) on B16 melanoma cells and Meth A sarcoma cells in a mice model in vivo, and on fibroblastic tumor cells, LS174T (colon-) carcinoma cells and Jurkat (leukemic-) cells in vitro (International Patent PCT No. PCT/EP91/01269, International Publication Number WO 92/00743 PCT "Use of Taurolidine and/or Taurultam for the treatment of tumors").

In systemic chemotherapy, the antineoplastic agent is unspecifically distributed throughout the body via circulation. Proliferating cells in healthy organs are thus exposed to the same concentrations of the agent as tumor cells. Moreover, intratumoral distribution of the agent may be prevented by different hemodynamic factors in the tumor. The antineoplastic action of most chemotherapeutic agents depends on the different in proliferation rates between normal cells and tumor cells. When these rates are the same, dose-limiting adverse events may occur. It is generally assumed that the effectiveness of chemotherapy increases with the concentration of the agent within the tumor and the duration of exposure. On the other hand, systemic administration is limited by the severity of adverse events.

An approach to overcome this problem is to administer chemotherapeutic agents locally relying on diffusion for their distribution. In local therapy, the antineoplastic agent is introduced into the tumor itself or the area around the tumor. The resulting pressure gradient leads to diffusion of the antineoplastic agent into the tumor. This mode of administration not only increases the concentration of the agent within the tumor but also results in much lower concentrations in other tissues compared to systemic administration.

Various materials such as collagen or biodegradable polymers or silicons used in local drug delivery systems. The materials serve as matrices by means of which embedded local cytostatic agents such as BCNU, mitoxantrone, or cisplatin are introduced into the tumor resection cavity. Moreover, silicones have been used for local delivery of antineoplastic agents. Potential problems with this mode of drug administration may arise when the carrier matrix contains components that undergo complete degradation after a very long time only or not at all. Another risk is the uncontrolled distribution of the antitumor agent in the CSF, which moreover, makes it difficult to accurately determine the concentration at the target. The postoperative changes in the shape and size of the tumor resection cavity associated with edema formation may preclude complete filling of the cavity with the drug-carrying wafers. The resulting inhomogeneous distribution of the agent can lead to pronounced local increases in drug concentration that may have toxic effects on adjacent healthy tissue.

Another approach of local tumor treatment is so-called convection-enhanced drug delivery (CEED) in which the drug is infused into the tumor or the surrounding brain. The drug is distributed by convective transport. However, this mode of administration requires placement of a catheter in most cases, which increases the risk of infection and the incidence of postoperative CSF fistula formation. Furthermore, it is better suited in cases of non-resected tumors. It can hardly be applied following tumor resection.

There remains a need in the art for new methods and compositions for treating tumors.

SUMMARY OF THE INVENTION

In accordance with the present invention, an antineoplastic composition is provided. The antineoplastic composition comprises an antineoplastic-effective amount of a methylol transfer agent (MTA) in combination with a biodegradable adhesive capable of adhering to tissue of a living subject.

DETAILED DESCRIPTION OF THE INVENTION

Methylol transfer agents, such as the antibacterial and antitoxin drug taurolidine and the related product taurultam, have been shown to exert a modifying effect on the toxicity of tumor necrosis factor (TNF) which is used, inter alia, in the treatment of tumors. Furthermore, the action of methylol transfer agents has been shown to be selective in that the growth of normal cell-lines was not significantly inhibited.

Taurolidine acts by transferring three methylol groups at the site of action, taurultam being an intermediate metabolite which itself transfers a single methylol group with liberation of the very well tolerated compound taurinamide and ultimately taurin. Taurin is an amino acid that is present in the body in large quantities, especially in the heart and in the brain.

It should be noted that methylol transfer is to be contrasted with methyl transfer which is characteristic of many highly toxic anti-tumor drugs. Taurolidine and taurultam have low toxicity and are not cytotoxic against normal cells.

The method is carried out by administering to a subject, e.g., a mammal suffering from cancer, compositions containing an active methylol-containing compound, at a dose sufficient to induce death of neoplastic cells by apoptosis. By "methylol-containing compound," or "methylol transfer agent," is meant a compound which contains or is capable of producing a methylol molecule under physiological conditions. A methylol-containing compound is characterized as having a R—N—CH2-OH group in which R is an alkyl, aryl or hetero group. The invention also includes the use of compounds capable of producing or being converted into a compound containing a R—N—CH2-OH structure.

Methylol transfer agents include methylol-containing compounds such as taurolidine, and taurultam, their derivatives, and organic or inorganic salts thereof. The compounds taurolidine and taurultam are disclosed in U.S. Pat. No. 5,210,083. Other suitable methylol-containing compounds include taurin derivatives, taurinamide derivatives, urea derivatives, organic or inorganic salts thereof. Examples of derivatives of taurolidine, taurultam, taurinamide and urea useful in the present invention can be found in WO 01/39763A2. Particularly preferred methylol transfer agents for utilization in accordance with the present invention are taurolidine, taurultam, biologically active derivatives thereof and mixtures thereof.

Alternatively, the compound is a taurinamide derivative, or a urea derivative. Examples of derivatives of taurolidine, taurultam, taurinamide and urea useful in the present invention can be found in WO 01/39763A2.

By derivative of taurolidine or taurultam is meant a sulfonamide compound which possesses at least 10% of the neoplastic activity of taurolidine or taurultam, respectively. A sulfonamide compound is one having a R2N—SO2R' formula. Derivatives of the compounds described herein may differ structurally from a reference compound, e.g., taurolidine or taurultam, but preferably retain at least 50% of the biological activity, e.g., induction of apoptotic cell death, of the reference compound. Preferably, a derivative has at least 75%, 85%, 95%, 99% or 100% of the biological activity of the reference compound. In some cases, the biological activity of the derivative may exceed the level of activity of the reference compound. Derivatives may also possess characteristics or activities not possessed by the reference compound. For example, a derivative may have reduced toxicity, prolonged clinical half-life, or improved ability to cross the blood-brain barrier.

Cancers to which the present invention may be applicable include recurrent glioblastoma, glioma, neuroblastoma, astrocytoma, carcinomatous meningitis, ovarian cancer, prostate cancer, central nervous system (CNS) cancer, lung cancer, gastric cancer, esophageal cancer, urinary bladder cancer, leukemia, mesothelioma, lymphoma, melanoma, renal cell cancer and metastases thereof. Other cancers against which the method of the present invention is effective include other carcinomas, sarcomas or lymphomas, cancers of the head and neck, liver cancer, breast cancer and pancreatic cancer.

Particularly preferred embodiments involve treatment of central nervous system (CNS) cancers, as well as inhibition of tumor metastases thereof.

The invention provides a method of treatment for preventing or inhibiting growth cancer cells, comprising applying an antineoplastic composition to tissue of a living subject in need of such treatment. The antineoplastic composition comprises an antineoplastic-effective amount of a methylol transfer agent (MTA) in combination of a biodegradable adhesive capable of adhering to tissue of a living subject. When used herein, the term biodegradable is intended to encompass bioabsorbable or errodable adhesives. In preferred embodiments, the inventive composition initially is in a fluid or semi-fluid state, most preferably in a liquid or semi-liquid state.

In preferred embodiments, the inventive composition is applied following at least partial extirpation of primary and/or secondary brain tumors or other tumors of the central nervous system (CNS). Other preferred applications are for the treatment of skin tumors, tumors in the mouth/jaw/face region, squamos cell carcinoma, tumors in the urogenital area, tumors of the outer eye and the eyelids, bone tumors, tumors of the parenchymatous organs, and tumors of the gastrointestinal tract.

In preferred embodiments, after at least partial removal of a tumor from an area of tissue of a living subject, the composition the present invention is applied to the area of tissue in a layer, preferably by spraying or brushing the composition onto the surface area of the cavity resulting from removal of the tumor.

As noted above, preferably the inventive composition initially is in a liquid or a semi-liquid state when it is applied and adhered to the area of tissue from which the tumor has been removed. In particularly preferred embodiments, after application, the adhesive increases in viscosity or at least partially solidifies while adhering to the tissue.

As noted above, in accordance with one aspect, the inventive composition is applied to the area in a layer, most preferably by spraying or with a brush. In accordance with one embodiment the layer has a thickness of about 0.1-10 mm, preferably about 1-5 mm, and most preferably about 1.5-2.5 mm.

In preferred embodiments, the methylol transfer agent is at a concentration in the inventive composition within a range of about 0.1-99% by weight, more preferably about 0.5-80% by weight still more preferably about 2-80% by weight, and even more preferably about 3-80% by weight. In other embodiments, the MTA concentration in the inventive composition is about 0.1-160 mg/ml, preferably at a concentration of about 20-100 mg/ml and more preferably at a concentration of about 50-80 mg/ml.

In preferred embodiments, the adhesive utilized in the present invention is a fibrin sealant matrix (fibrin glue). Fibrin glue is a two-component system of separate solutions of fibrinogen and thrombin/calcium. When the two solutions are combined, the resultant mixture mimics the final stages of the clotting cascade to form a fibrin clot. The fibrinogen component can be prepared extemporaneously from autologous, single-donor, or pooled blood. Fibrin glue is available in Europe under the brand names Beriplast, Tissel, and Tissucol. Fibrin glue has been used in a wide variety of surgical procedures to repair, seal, and attach tissues in a variety of anatomic sites.

In particularly preferred embodiments, after application of a layer of the inventive composition over the area to be treated, the layer is covered and sealed with a sealing second layer which does not contain methylol transfer agent. The sealing second layer can be the same biodegradable adhesive utilized in the inventive composition, for example, a fibrin sealant matrix.

In other embodiments, the biodegradable adhesive utilized in the inventive composition is a gel (e.g., adhesive collagen gel), gel/fibrin mixture, powder or the like. For example, the MTA can be encapsulated in adhesive fibrin particles for sustained release of the MTA. Alternatively, microcapsules contain MTA can be suspended in the adhesive.

Malignant gliomas tend to recur in the vast majority of cases. Recurrent gliomas may arise from vital tumor cells present in this zone around the resection margin. Recurrent gliomas grow very rapidly, and quickly result in death of the patient. The present invention may combine tumor resection with local chemotherapy using an antineoplastic, but non-toxic agent. Taurolidine exerts a selective antineoplastic effect by induction of programmed cell death, and has anti-angiogenic activity. Fibrin sealant is completely degradable and firmly adheres to brain tissue, thereby providing a matrix for taurolidine delivery—a Taurolidine-Fibrin-Sealant-Matrix (TFM)—in the local treatment of brain tumors.

Taurolidine or other MTAs can be suspended homogeneously in both the thrombin and the procoagulant protein components of the fibrin sealant. The fibrin sealant matrix is a suitable carrier for the suspension of taurolidine or other MTAs at a concentration that ensures the release of therapeutically effective amounts of the drug over a period of up to two weeks or longer, in vitro. The antineoplastic action of taurolidine is not affected by embedding in the fibrin sealant matrix.

The inventive drug delivery system may be suitable for interoperatively local taurolidine treatment of brain tumors following complete or partial resection or of tumors that are non-resectable because of their location.

Malignant gliomas invade surrounding tissue and therefore tend to recur in the vast majority of cases even after apparently complete gross resection. Gliomas recur within 2 cm of the original resection margin in 80-90% of cases. Thus, recurrent gliomas may arise from vital tumor cells present in this zone around the resection margin. The extent of tumor resection correlates with postoperative survival. Furthermore, metastases from malignant gliomas are very rare and primarily extracerebral in location.

In accordance with one embodiment, total or partial tumor resection is combined local chemotherapy using an agent with a selective antineoplastic activity without damaging normal brain tissue. In accordance with one embodiment, a method for delivering the drug into the brain enables close contact to the tumor or the walls of the resection cavity. The method allows the delivery of the drug in therapeutically effective concentrations with minimal toxic effects on healthy brain tissue. Moreover, the method of delivery is devoid of the risk of infection and leaves no residue that may cause local complications.

Additionally, since the presence of taurin in the brain is abnormally low in glioblastoma patients, administration of taurolidine and/or taurultam has the additional advantage of raising the taurin level in the brain, since both compounds are ultimately metabolized into taurin.

Taurolidine has a double effect against tumors. It triggers the induction of programmed tumor cell death (apoptosis), and it also has anti-angiogenic activity by inhibiting VEGF and TGF beta. Simultaneous intravenous administration of an MTA such as taurolidine in patients with glioblastoma may also be utilized.

EXAMPLE

A fibrin sealant matrix was prepared using the Tissel kit (Immuno AG, Vienna, Austria, kindly provided by Baxter Deutschland GmbH, Heidelberg, Germany) according to manufacturer's instructions. Taurolidine (ultrapure) was kindly provided by Geistlich Pharma AG, Wolhusen, Switzerland.

Different concentrations of taurolidine were homogenously suspended in the two components of the fibrin sealant. The two components were then mixed in wells of a 24-multiwell plate to prepare matrixes with identical total volumes of 400 µl per well containing final taurolidine concentrations of 10, 20, 40 and 80 mg/ml. The resulting thickness of the matrix was 2 mm ±0.4 mm. In addition, matrices with volumes of 400 µl and 800 µl containing 10 mg/ml or 40 mg/ml of taurolidine were prepared to investigate the effect of matrix size on taurolidine release. The 800-µl matrix had a thickness of 4 mm ±0.3 mm. Matrices of identical volume and thickness without taurolidine served as controls. Supernatants of 400 µl phosphate-buffered saline (PBS) were added to each well after solidification. The multiwell plates were incubated at 37° C. The supernatants were pipetted off at 24-hour intervals over a period of 7 days and replaced by identical amounts of fresh PBS.

The long-term release kinetics of taurolidine was investigated by homogenously suspending different concentrations of taurolidine in the two components of the fibrin sealant in such a way that final concentrations (mg/ml) of 10, 40 and 80 mg/ml were achieved per 400 µl of fresh PBS at 24-hour intervals over a period of 14 days. The supernatants from the wells containing identical taurolidine concentrations were pooled. The taurolidine concentrations in the supernatants were determined.

To determine whether the antineoplastic activity of taurolidine was affected by embedding in the matrix, the glial tumor cell lines LN18, LN229, U87MG, and ex vivo cells from a freshly isolated glioblastoma were incubated with taurolidine released from the matrices at different periods.

The LN18, LN229, and U87MG tumor cells and ex vivo cells from a glioblastoma were seeded in 150 cm$^3$ plastic cell culture flasks until a cell confluency of 80% was reached. The resulting cell suspensions were centrifuged at 1200 rpm for 5 min and then diluted to yield cell suspensions containing $5 \times 10^4$ cells per ml. Aliquots of 200 µl of the cell suspensions were pipetted into the wells of a 96-multiwell plate.

After 12 hours when the cells were adherent the medium was removed and replaced by fresh medium. The cells were incubated for 24 hours and the taurolidine solution released at different time intervals from the matrices loaded with different taurolidine concentrations. Tumor cells incubated with the same volume of supernatant from fibrin sealant matrix without taurolidine were used as negative controls. Identically treated cells to which Fas-ligand at a concentration of 25% was added served as positive controls.

After incubation for 24 hours, the supernatants were removed and 100 µl of crystal violet staining solution (0.5% crystal violet in 19.5% methanol and 80% distilled water) added. The solution was removed after 10 min and residual dye rinsed off with tap water. The plates were then left to air-dry for 12 hours followed by counting in a microplate counter at 540 nm.

The theoretical assumptions underlying the diffusion-controlled release of taurolidine from the fibrin sealant matrix were reviewed. Using a model of local taurolidine metabolism, the factors affecting the diffusion-controlled release of taurolidine from the matrix were investigated.

The two components of the fibrin sealant containing the suspended taurolidine were sprayed through a single nozzle at 1.5 bar by means of filter-sterilized compressed air. The highest possible concentration of taurolidine in the matrix was investigated. It was determined whether a uniform distribution of the TFM could be achieved.

The investigation of taurolidine release from the fibrin sealant matrix over a period of 1 week showed an exponential increase of the cumulative amount of taurolidine released.

The cumulative amounts of taurolidine released into the supernatant at different concentrations of taurolidine loading differed statistically significantly [analysis of variance (ANOVA), Kruskal-Wallis-test; $p<0.001$]. The exponential course of cumulative taurolidine release from the matrix resulted in the largest amounts of taurolidine being released within the first days.

The temporal course of percentage taurolidine release was determined in relation to the initial taurolidine load of the matrix. The results suggested that, irrespective of the initial taurolidine concentration, about 50% of the total taurolidine was released from the matrix within the first 2 days (54.7±1.44%) and about 75% within 6 days (75.2±6.64%). The percentage release rates did not differ significantly for the different taurolidine loading concentrations in the TFM (ANOVA, Kruskal-Wallis-test; p=0.522).

Cumulative taurolidine release differed significantly for constant concentrations of taurolidine but different matrix volumes (ANOVA and Holm-Sidak-test; p<0.001) while no statistically significant differences in cumulative taurolidine release were seen for identical initial amounts of taurolidine in different matrix volumes (analysis of variance and Holm-Sidak-test; p=0.934 (initial amount of 8 mg) and p=0.159 (initial amount of 32 mg).

The loaded amount of taurolidine in the matrix seems to be the crucial determinant of release. Apparently, the thickness of the matrix does not have an important role in controlling taurolidine release. This observation is crucial for the practical application of the fibrin sealant matrix since it may not be possible ensure a uniform matrix thickness in all cases.

A long life span of the TFM is desirable to ensure local therapy over an adequate period of time. The life span of a fibrin matrix is limited by the onset of fibrinolysis. The data available so far suggest that the in vivo life span can at most be extended to 12-14 days when an antifibrinolytic, such as aprotinin is added. Moreover, the rate at which the fibrin sealant matrix is degraded varies with the proteolytic activity at the site of application.

We therefore investigated whether taurolidine is released throughout the maximum life span of the matrix of 14 days. In the experimental model used here, antineoplastically effective amounts of taurolidine were released throughout the 14-day observation period at the loading concentrations of taurolidine to 25 mg/ml, or above. Loading concentrations of 50 mg/ml or higher resulted in the release of over 100 µg/ml of taurolidine on day 14. This taurolidine level is above the $EC_{50}$ of acute cytotoxicity for most of the cell lines tested with taurolidine before.

The temporal course of taurolidine release was investigated for different loading amounts of taurolidine in the matrix over a period of 14 days. Irrespective of loading concentrations, 98.93%±0.33 of the taurolidine had been released from the matrix after 10 days and almost 100% (99.99%±0.02) after 14 days. The percent release did not change for the different loading concentrations of taurolidine (ANOVA, Kruskal-Wallis test; p=0.830).

The proliferation of all the tumor cell lines investigated, and of the ex vivo glioblastoma cells was inhibited in an concentration-dependent manner. Taurolidine released on day 13 from TFM with an initial taurolidine loading concentration of 10 mg/ml had no further effects on tumor cell proliferation. This is in accordance with the concentration of taurolidine released from the matrix at this time. In contrast, taurolidine released on day 3 with a loading concentration of 100 mg/ml was found to reduce cell counts by at least 60%.

The taurolidine-loaded fibrin sealant matrix was applied intraoperatively after removal of the tumor in a way to ensure close binding to the wall of the cavity and filling out all the surface irregularities. Taurolidine then diffused from the matrix compartment into the brain compartment along the diffusion gradient, which is the main force underlying taurolidine release. At the same time, the process of elimination of taurolidine from the brain area adjacent to the matrix starts; by metabolism, on one hand, and by diffusion into deeper brain areas, on the other hand.

In addition to these processes, taurolidine may enter and get distributed in the cerebrospinal fluid (CSF) space. This distribution is driven by diffusion through the matrix surface facing the resection cavity and enhanced by CSF convection, particularly when the resection cavity remains "open". To counteract these undesired losses, a multilayer matrix was applied, with the top layer comprising fibrin sealant without taurolidine. This extra layer reduced the loss of drug due to diffusion into and convection of CSF. Losses of drug by the route were taken into consideration by using a safety factor in calculating taurolidine delivery.

The TFM undergoes fairly little dissolution or erosion and therefore released the suspended drug it carries primarily by diffusion. The release is dominated by the diffusion velocity of the drug from the matrix into surrounding tissue. The release rates under these conditions, are in linear relationship to the square root of time.

The amount of taurolidine released from the matrix is directly proportional to the diffusion area. Therefore, a proportionality factor for the different initial concentrations of taurolidine in the matrix is determined, which then can be sued to calculate taurolidine release as a function of time and diffusion area.

The experimental results and the calculated data showed no statistically significant differences for any of the initial taurolidine concentrations investigated.

TFM releases of taurolidine were sufficient in concentration to exert antitumor activity over 14 days. The results of the in vitro experiments suggest that an initial taurolidine concentration of 80 mg/ml is appropriate.

The required matrix volume was calculated from the amount of taurolidine released and the initial taurolidine concentration, $c_0$, according to the equation:

$$V_{TFM} = \frac{M(1+k_s)}{C_0},$$

where $V_{TFM}$=required TFM volume [ml]; M=cumulative amount of taurolidine released [mg]; $k_s$=safety factor; $c_0$=initial taurolidine concentration in the TFM [mg/ml]. The safety factor was introduced to compensate for diffusion losses into the fibrin sealant cover layer and subsequent losses by convention. The safety factor chosen was 1.

The TFM was applied to the resection cavity of spraying. Application by spraying facilitates even distribution of the matrix on the walls of the resection cavity. Suspension of taurolidine in the two components of the fibrin sealant and spraying of the drug delivery system posed no problems for initial taurolidine loading concentrations of up to 80 mg/ml. It was possible to apply TFM very homogenously and even in multiple layers due to the short coagulation time.

The limitations of prior art local drug administration can be overcome by the method of MTA (e.g., taurolidine) administration in an adhesive as disclosed herein. This matrix is sprayed over the walls of the resection cavity after total or partial tumor resection. During coagulation, fibrinogen is converted into fibrin and forms covalent bonds with surrounding proteins, resulting in a layer of hemostatically active sealant that is subsequently degraded by proteolytic activity. This matrix has hemostatic effects necessary after surgery. On the other hand, covalent bonding to surrounding proteins ensures that the matrix stays exactly where it has been applied. This is crucial since the displacement of brain structures after tumor resection and postoperative edema formation change the size and the shape of the resection cavity.

The experimental results demonstrate that the taurolidine is released from the TFM under infinite-sink conditions over 2 weeks in concentrations that have definitive antineoplastic effects on the tumor cell lines and ex vivo tumor cells investigated here. A study investigating the release of antibiotics from a fibrin matrix suggests that the limited-sink model is most suitable to describe the in vivo conditions. The experiments using different tumor cell lines and ex vivo glioblastoma cells show that the antitumor activity of taurolidine is not affected by its embedding in the fibrin sealant matrix. Taurolidine is known to have no cytotoxic effects on normal cells. Earlier cell culture experiments using neuronal and glial brain cells obtained from rat fetuses on day 15 of gestation showed that taurolidine has no cytotoxic effects on these cells. A taurolidine concentration of 80 mg per ml of fibrin sealant an be homogenously suspended in the matrix.

A fibrin matrix is a suitable carrier for the suspension of taurolidine at a concentration that ensures the release of therapeutically effective amounts of the drug over a period of 2 weeks in vitro. The antineoplastic action of taurolidine is not affected by embedding in and release from fibrin sealant matrix. Higuchi's model of drug release from matrices provides a suitable approximation for describing the diffusion-controlled release of taurolidine from the fibrin sealant matrix.

The described drug delivery system is suitable for local taurolidine treatment of brain tumors following complete or partial resection or of tumors that are non-resectable because of their location.

The invention claimed is:

1. An antineoplastic composition comprising an antineoplastic-effective amount of a methylol transfer agent (MTA) comprising taurolidine, taurultam or a mixture thereof, in combination with a biodegradable adhesive comprising a fibrin sealant matrix capable of adhering to tissue of a living subject, said composition being prepared with said MTA at a final MTA concentration of at least about 20 mg/ml and no higher than 160 mg/ml.

2. The composition of claim 1 wherein said MTA of said composition is at a concentration of at least about 25 mg/ml and no higher than 160 mg/ml.

3. A system for preventing or inhibiting growth of cancer cells in a subject, comprising the antineoplastic composition of claim 1, in combination with an intravenously administrable composition, comprising taurolidine, taurultam or a mixture thereof for intravenous administration to said subject.

4. The composition of claim 1 wherein said fibrin sealant matrix comprises separate thrombin and procoagulant protein components, and said taurolidine, taurultam mixture thereof is suspended in both of said components.

* * * * *